United States Patent [19]

Fayerman et al.

[11] Patent Number: 4,643,975

[45] Date of Patent: Feb. 17, 1987

[54] NOVEL CLONING VECTORS FOR USE IN STREPTOMYCES, ESCHERICHIA COLI AND RELATED ORGANISMS

[75] Inventors: Jeffrey T. Fayerman, Indianapolis, Ind.; Nancy E. Malin, Mountain View, Calif.

[73] Assignee: Eli Lilly and Company, Indianapolis, Ind.

[21] Appl. No.: 568,179

[22] Filed: Jan. 5, 1984

[51] Int. Cl.[4] .................. C12N 1/00; C12N 15/00; C12P 21/00

[52] U.S. Cl. .................................. 435/317; 435/68; 435/172.3; 935/29; 935/75

[58] Field of Search ................ 435/317, 68, 172.3; 935/22, 27, 23, 29, 75, 66

[56] References Cited

U.S. PATENT DOCUMENTS 4,332,900  6/1982  Manis et al. ..................... 435/172

4,513,086  4/1985  Fayerman et al. ................. 435/317

FOREIGN PATENT DOCUMENTS 2107716  5/1983  United Kingdom ............. 435/172.3

OTHER PUBLICATIONS

Thompson, C. et al., 1980, Nature 286:525.
Hopwood, D. A. et al., 1983, Trends in Biotechnology, 1:42.
Richardson, M. et al., 1982, Gene 20:451.

Primary Examiner—Thomas G. Wiseman
Assistant Examiner—Joanne M. Giesser
Attorney, Agent, or Firm—Lisabeth F. Murphy

[57] ABSTRACT

The present invention discloses novel selectable recombinant DNA cloning vectors for use in Streptomyces, E. coli and related organisms. The invention further comprises transformants of the aforementioned vectors.

34 Claims, 7 Drawing Figures

Restriction Site and Function Map of
Plasmid pFJ258
(10 kb)

Restriction Site Map of Plasmids
pLR 1, pLR 2 and pLR 4

Restriction Site and Functional Map of Plasmids pFJ127 and pFJ277 pFJ127 pFJ277

Restriction Site and Functional Map of Plasmids pFJ278 and pFJ279

Restriction Site and Functional Map
of Plasmid pFJ282** pFJ282

Restriction Site and Functional Map
of Plasmids pFJ141 and pFJ142**

Restriction Site and Functional Map of Plasmids pFJ291 and pFJ292 pFJ291 pFJ292

NOVEL CLONING VECTORS FOR USE IN STREPTOMYCES, ESCHERICHIA COLI AND RELATED ORGANISMS

SUMMARY OF THE INVENTION

The present invention comprises novel recombinant DNA cloning vectors comprising a functional Streptomyces origin of replication-containing restriction fragment of plasmid pFJ258 and one or more DNA segments that convey resistance to antibiotics. The invention further comprises transformants of the aforementioned vectors.

The present invention provides antibiotic resistance conferring cloning vectors for use in Streptomyces and related host cells. Heretofore, the development and exploitation of recombinant DNA technology in the above organisms has been retarded and made especially difficult because of the general lack of selectable genetic markers on cloning vectors. The vectors of the present invention are functional and selectable in both Streptomyces and other host strains and therefore represent a significant advance in the technical art.

The present vectors are particularly useful because they are relatively small, versatile, and can transform and be selected in any Streptomyces cell that is sensitive to an antibiotic for which resistance is conveyed. Since seventy percent of naturally occurring antibiotics are produced by Streptomyces strains, it is desirable to develop cloning systems and vectors that are applicable to that industrially important group. The present invention provides such vectors and thus allows for the cloning of genes into Streptomyces both for increasing the yields of known antibiotics as well as for the production of new antibiotics and antibiotic derivatives.

The present invention provides vehicles for cloning DNA into Streptomyces host cells and also allows for the convenient selection of transformants. Since transformation is a very low frequency event, such a functional test is a practical necessity for determining which cell(s), of among the billions of cells, has acquired the plasmid DNA. This is important because DNA sequences that are themselves non-selectable can be inserted into the vectors and, upon transformation, cells containing the vector and the particular DNA sequence of interest can be isolated by appropriate antibiotic selection.

For purposes of the present invention as disclosed and claimed herein, the following terms are as defined below.

Recombinant DNA Cloning Vector—any autonomously replicating agent, including but not limited to plasmids, comprising a DNA molecule to which one or more additional DNA segments can or have been added.

Transformation—the introduction of DNA into a recipient host cell that changes the genotype and consequently results in a stable and heritable change in the recipient cell.

Transformant—a recipient host cell that has undergone transformation.

Sensitive Host Cell—a host cell that cannot grow in the presence of a given antibiotic without a DNA segment that confers resistance thereto.

Restriction Fragment—any linear DNA generated by the action of one or more restriction enzymes on plasmid or chromosomal DNA.

Plasmid pLR2 ~1.6 kb BamHI Restriction Fragment—the same ~1.6 kb BamHI thiostrepton resistance-conferring fragment contained in plasmid pIJ6.

Plasmid pLR2 ~0.8 kb BclI Restriction Fragment—the same ~0.8 kb BclI thiostrepton resistance-conferring fragment contained in plasmid pIJ6.

Plasmid pLR1 or pLR4 ~3.4 kb BamHI Restriction Fragment—the same ~3.4 kb BamHI neomycin resistance-conferring fragment contained in plasmid pIJ2.

$Amp^R$—the ampicillin resistant phenotype.
$Cm^R$—the chloramphenicol resistant phenotype.
$Tet^S$—the tetracycline sensitive phenotype.
$Thio^R$ or tsr—the thiostrepton resistant phenotype.
$Neo^R$—the neomycin resistant phenotype.

DETAILED DESCRIPTION OF THE INVENTION

The present invention comprises recombinant DNA cloning vectors comprising:
(a) a functional Streptomyces origin of replication-containing restriction fragment of plasmid pFJ258, and
(b) one or more DNA segments that convey resistance to at least one antibiotic when transformed into a sensitive host cell that is susceptible to transformation, cell division, and culture.

The invention further comprises transformants of the aforementioned vectors.

Figure 1:
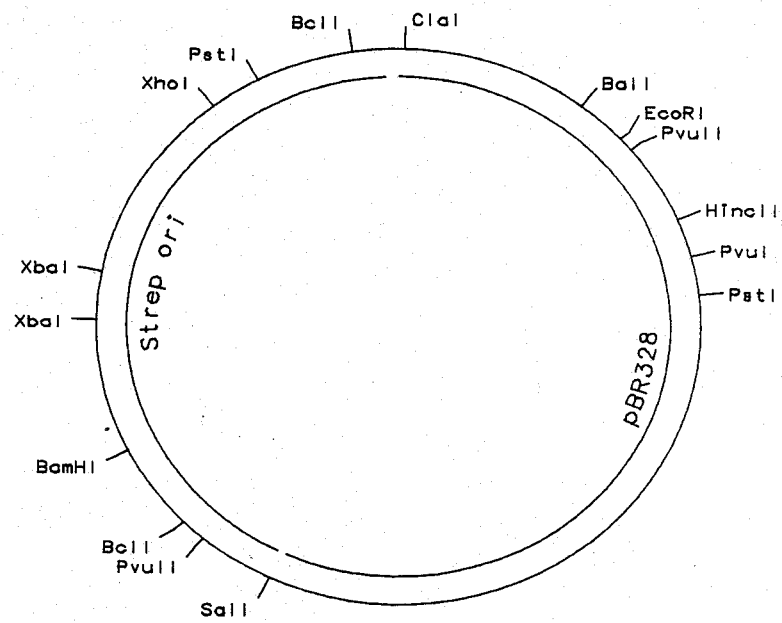

The vectors of the present invention are constructed by ligating one or more antibiotic resistance-conferring DNA segments into an Streptomyces origin of replication-containing restriction fragment of plasmid pFJ258. Plasmid pFJ258, from which the origin of replication-containing fragments are constructed, is approximately 10 kb and contains several restriction sites which are particularly advantageous for molecular cloning. Since the Streptomyces origin of replication of plasmid pFJ258 has been localized to within the ~2.23 kb XbaI-BclI restriction fragment, a variety of different origin of replication containing fragments can be generated by digesting the plasmid with restriction enzymes that cut outside the ~2.23 kb Xba-BclI region. A detailed restriction site map of plasmid pFJ258 is presented in FIG. 1 of the accompanying drawings. For purposes of the present application, FIG. 1 and all subsequent figures are not drawn to scale.

Plasmid pFJ258 can be conventionally isolated from *Escherichia coli* K12 HB101/pFJ258, a strain deposited and made part of the permanent stock culture collection of the Northern Regional Research Laboratory, Peoria, Ill. The strain is available to the public, as a preferred source and stock reservoir of the plasmid, under the accession number NRRL B-15262.

Although many different Streptomyces origin of replication-containing fragments of plasmid pFJ258 can be constructed, those exemplified herein for illustrative purposes include the ~3.64 kb SalI-BclI, ~2.23 kb XbaI-BclI, and the ~2.85 kb BamHI-BclI restriction fragments. These fragments can be independently ligated to one or more antibiotic resistance-conferring DNA fragments, exemplified herein for illustrative purposes by the thiostrepton resistance-conferring ~1.6 kb BamHI restriction fragment of plasmid pLR2 and subfragments thereof, and the neomycin resistance-conferring ~3.4 kb BamHI restriction fragment of plasmid pLR1 or plasmid pLR4, to form vectors illustrative of the present invention.

Figure 2:
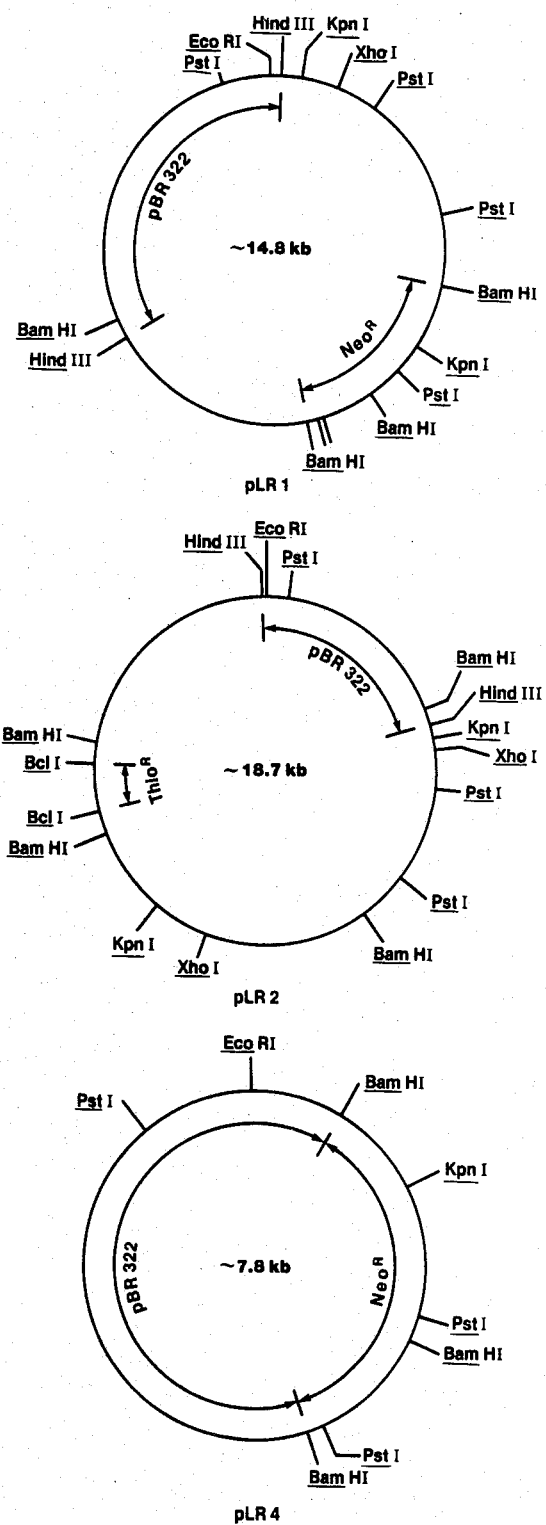

Plasmid pLR2, the source of the thiostrepton resistance-conferring fragment, is approximately 18.7 kb and is constructed by ligating HindIII treated plasmid pIJ6, disclosed in Thompson et al., 1980, Nature 286:525, to HindIII treated plasmid pBR322. Plasmid pLR1, the source of the neomyoin resistance-conferring fragment, is approximately 14.8 kb and is similarly constructed, except that plasmid pIJ2, disclosed in Thompson et al., 1980, is used instead of plasmid pIJ6. Both plasmids pLR2 and pLR1 are functional in *E. coli* and therefore can be amplified and isolated conveniently for subsequent manipulation. An analogous construction, resulting in plasmid pLR4, is made by ligating BamHI treated plasmid pBR322 to BamHI treated plasmid pLR1. A restriction site and functional map of each of plasmids pLR1, pLR2, and pLR4 is presented in FIG. 2 of the accompanying drawings.

For convenience and ease of construction, the thiostrepton resistance-conferring ~1.6 kb BamHI fragment and subfragments thereof, and the neomycin resistance-conferring ~3.4 kb BamHI fragment are ligated to the ~2.23 kb XbaI-BclI origin of replication-containing fragments of plasmid pFJ258. The resulting recombinant DNA is then ligated to produce plasmids illustrative of the present invention. Recombinant plasmids of two orientations may result depending upon the orientation of the particular resistance-conferring DNA fragment or subfragment. Thus, ligation of the ~0.8 kb BclI fragment of plasmid pLR2 into the ~2.23 kb XbaI-BclI fragment of plasmid pFJ258 results in illustrative plasmids pFJ295 and pFJ296; ligation of the ~3.4 kb BamHI fragment of plasmid pLR1 or plasmid pLR4 results in illustrative plasmids pFJ297 and pFJ298; and ligation of both of the fragments results in illustrative plasmids pFJ299, pFJ300, pFJ303, and pFJ304.

The ligations used to construct illustrative plasmids pFJ291 and pFJ292 are made possible by the fact that some restriction enzymes, such as BclI and BamHI, generate compatible cohesive ends. However, in a few cases, fragments generated by one restriction enzyme when ligated to fragments generated by a second enzyme give rise to hybrids that are recognized by neither of the parental enzymes. For example, when fragments generated by BclI (T ↓ GATCA) are ligated to fragments generated by BamHI (G ↓ GATCC), the resulting hybrid target sites, hereinafter designated as [BclI/-BamHI], are cleaved by neither BclI nor BamHI.

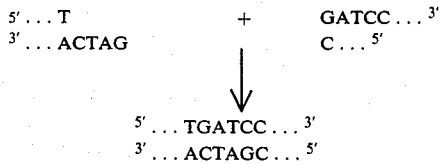

Thus, although these target sites are nonfunctional for subsequent restrictions, this construction preserves the unique BamHI or BclI restriction site as found on the parental plasmid.

Various plasmid pFJ258 restriction fragments can be used for the ligation to antibiotic resistance-conferring DNA segments provided that the Streptomyces origin of replication contained in the ~2.23 kb XbaI-BclI restriction fragment is present. Additional plasmid pFJ258 restriction fragments, useful for constructing illustrative plasmids within the scope of the present invention, include, but are not limited to, the XbaI and BamHI fragments. The single PstI site within the ~2.23 kb XbaI-BclI restriction fragment of plasmid pFJ258 is required for replication and is therefore unavailable for cloning. A particular antibiotic resistance-conferring DNA segment is not limited to a single position on a plasmid pFJ258 fragment but can be ligated or inserted into varying sites provided that the origin of replication or other critical plasmid controlled physiological functions are not disrupted. Those skilled in the art understand or can readily determine which sites are advantageous for the ligation or insertion of a particular DNA segment.

Although the thiostrepton and neomycin antibiotic resistance-conferring DNA segments exemplified herein are respectively the ~1.6 kb and ~3.4 kb BamHI restriction fragments of plasmids pLR2 and pLR1 and the ~0.8 kb BclI restriction fragment or plasmid pLR2, those skilled in the art can construct and use, either individually or in combination, additional DNA segments that also confer resistance to thiostrepton and neomycin. An additional thiostrepton resistance-conferring DNA segment of plasmid pLR2 can be, for example, the ~13 kb PstI restriction fragment. Additional neomycin resistance-conferring DNA segments of plasmid pLR1 include, for example, the ~3.5 kb PstI restriction fragment and also the larger of the SstI-KpnI subfragments of the ~3.4 kb BamHI restriction fragment.

Still other DNA segments that confer resistance to the same or to different antibiotics such as, for example, chloramphenicol, streptomycin, hygromycin, puromycin, viomycin, tylosin, erythromycin, vancomycin, actaplanin, and the like can also be constructed and used by those skilled in the art.

Functional derivatives of the various antibiotic resistance-conferring DNA segments can be made by adding, eliminating, or substituting certain nucleotides in accordance with the genetic code. Those skilled in the art will understand that ligation of these modified segments, or any other antibiotic resistance-conferring DNA segment, to an Streptomyces origin of replication-containing fragment of plasmid pFJ258 results in vectors that are also within the scope of the present invention.

Derivative vectors that further exemplify the invention can also be constructed. For example, XbaI deletion of plasmid pFJ127 results in illustrative plasmid pFJ282, a plasmid from which additional derivatives can also be made. Thus, insertion of the plasmid pLR1 or pLR4 ~3.4 kb BamHI neomycin resistance-conferring fragment into plasmid pFJ282 results in illustrative plasmids pFJ283 and pFJ284. The aforementioned antibiotic resistance-conferring derivative plasmids contain the plasmid pFJ258 Streptomyces origin of replication and are therefore within the scope of the present invention.

The restriction fragments of plasmid pFJ258 and the various antibiotic resistance-conferring DNA can be modified to facilitate ligation. For example, an XbaI-BclI molecular linker can be provided to the ~2.23 kb XbaI-BclI plasmid pFJ258 restriction fragment which has been previously ligated to the ~0.8 kb BclI thiostrepton resistance-conferring segment of pLR2 and then ligated to circular form to create illustrative plasmids pFJ299 and pFJ300. Synthetic linkers can be provided such that the restriction sites are left functionally intact after ligation for subsequent restrictions. Thus, plasmids pFJ299 and pFJ300 contain functional XbaI and BclI restriction sites. In addition, plasmid pFJ258 and the pFJ258 origin of replication-containing restriction fragments can also be modified by adding, eliminating, or substituting certain nucleotides to alter characteristics and to provide a variety of restriction sites for ligation of DNA. Those skilled in the art understand nucleotide chemistry and the genetic code and thus which nucleotides are interchangeable and which DNA modifications are desirable for a specific purpose.

The present Streptomyces-functional vectors such as, for example, plasmids pFJ127, pFJ278, pFJ282, pFJ283, pFJ291, pFJ295, pFJ297 and pFJ299 can be ligated to a functional replicon-containing and antibiotic resistance-conferring restriction fragment of a variety of E. coli plasmids such as, for example, plasmids pBR322, pBR325, pBR328 and the like, to produce self-replicating bifunctional vectors that are selectable in both E. coli and Streptomyces.

These bifunctional constructions comprise the pFJ258 Streptomyces origin of replication, a DNA segment that confers antibiotic resistance in Streptomyces, a replicon that is functional in E. coli and also a DNA segment that confers antibiotic resistance in E. coli. Bifunctional constructions, exemplified herein by plasmids pFJ141, and pFJ142 are particularly advantageous because amplification and manipulation of plasmids can be done faster and more conveniently in E. coli than in Streptomyces. Thus, after desired recombinant DNA procedures are accomplished within the E. coli host system, the entire plasmid or the particular Streptomyces DNA can be removed, and re-constructed (if necessary) to plasmid form, and then transformed into a Streptomyces or related host cell.

The recombinant DNA cloning vectors of the present invention are not limited for use in a single species or strain of Streptomyces. To the contrary, the vectors are broadly applicable and can be transformed into host cells of many Streptomyces taxa, particularly restrictionless strains of economically important taxa that produce antibiotics such as aminoglycoside, macrolide, β-lactam, polyether, and glycopeptide antibiotics and the like. Such restrictionless strains are readily selected and isolated from Streptomyces taxa by conventional procedures well known in the art (Lomovskaya et al., 1980, Microbiological Reviews 44:206). Host cells of restrictionless strains lack restriction enzymes and therefore do not cut or degrade plasmid DNA upon transformation. For purposes of the present application, host cells containing restriction enzymes that do not cut any of the restriction sites of the present vectors are also considered restrictionless.

Preferred host cells of restrictionless strains of Streptomyces taxa that produce aminoglycoside antibiotics and in which the present vectors are especially useful and can be transformed, include restrictionless cells of, for example: S. kanamyceticus (kanamycins), S. chrestomyceticus (aminosidine), S. griseoflavus (antibiotic MA 1267), S. microsporeus (antibiotic SF-767), S. ribosidificus (antibiotic SF733), S. flavopersicus (spectinomycin), S. spectabilis (actinospectacin), S. rimosus forma paromomycinus (paromomycins, catenulin), S. fradiae var. itallcus (aminosidine), S. bluensis var. bluensis (bluensomycin), S. catenulae (catenulin), S. olivoreticuli var. cellulophilus (destomycin A), S. tenebrarius (tobramycin, apramycin), S. lavendulae (neomycin), S. albogriseolus (neomycins), S. albus var. metamycinus (metamycin), S. hygroscopicus var. sagamiensis (spectinomycin), S. bikiniensis (streptomycin), S. griseus (streptomycin), S. erythrochromogenes var. narutoensis (streptomycin), S. poolensis (streptomycin), S. galbus (streptomycin), S. rameus (streptomycin), S. olivaceus (streptomycin), S. mashuensis (streptomycin), S. hygroscopicus var. limoneus (validamycins), S. rimofaciens (destomycins), S. hygroscopicus forma glebosus (glebomycin), S. fradiae (hybrimycins neomycins), S. eurocidicus (antibiotic A16316-C), S. aquacanus (N-methyl hygromycin B), S. crystallinus (hygromycin A), S. noboritoensis (hygromycin), S. hygroscopicus (hygromycins), S. atrofaciens (hygromycin), S. kasugaspinus (kasugamycins), S. kasugaensis (kasugamycins), S. netropsis (antibiotic LL-AM31), S. lividus (lividomycins), S. hofuensis (seldomycin complex), and S. canus (ribosyl paromamine).

Preferred host cells of restrictionless strains of Streptomyces taxa that produce macrolide antibiotics and in which the present vectors are especially useful and can be transformed, include restrictionless cells of, for example: S. caelestis (antibiotic M188), S. platensis (platenomycin), S. rochei var. volubilis (antibiotic T2636), S. venezuelae (methymycins), S. griseofuscus (bundlin), S. narbonensis (josamycin, narbomycin), S. fungicidicus (antibiotic NA-181), S. griseofaciens (antibiotic PA133A, B), S. roseocitreus (albocycline), S. bruneo-griseus (albocycline), S. roseochromogenes (albocycline), S cinerochromogenes (cineromycin B), S. albus (albo-mycetin), S. felleus (argomycin, picromycin), S. rochei (lankacidin, borrelidin), S. violaceoniger (lankacidin), S. griseus (borrelidin), S. maizeus (ingramycin), S. albus var. coilmyceticus (coleimycin), S. mycarofaciens (acetyl-leukomycin, espinomycin), S. hygroscopicus (turimycin, relomycin, maridomycin, tylosin, carbomycin), S. griseospiralis (relomycin), S. lavendulae (aldgamycin), S. rimosus (neutramycin), S. deltae (deltamycins), S. fungicidicus var. espinomyceticus (espinomycins), S. furdicidicus (mydecamycin), S. ambofaciens (foromacidin D), S. eurocidicus (methymycin), S. griseolus (griseomycin), S. flavochromogenes (amaromycin, shincomycins), S. fimbriatus (amaromycin), S. fasciculus (amaromycin), S. erythreus (erythromycins), S. antibioticus (oleandomycin), S. olivochromogenes (oleandomycin), S. spinichromogenes var. suragaoensis (kujimycins), S. kitasatoensis (leucomycin), S. narbonensis var. josamyceticus (leucomycin A3, josamycin), S. albogriseolus (mikonomycin), S. bikiniensis (chalcomycin), S. cirratus (cirramycin), S djakartensis (niddamycin), S. eurythermus (angolamycin), S. fradiae (tylosin, lactenocin, macrocin), S. goshikiensis (bandamycin), S. griseoflavus (acumycin), S. halstedii (carbomycin), S. tendae (carbomycin), S. macrosporeus (carbomycin), S. thermotolerans (carbomycin), and S. albireticuli (carbomycin).

Preferred host cells of restrictionless strains of Streptomyces taxa that produce β-lactam antibiotics and in which the present vectors are especially useful and can be transformed, include restrictionless cells of, for example: S. lipmanii (A16884, MM4550, MM13902), S. clavuligerus (A16886B, clavulanic acid), S. lactamdurans (cephamycin C), S. griseus (cephamycin A, B), S. hygroscopicus (deacetoxycephalosporin C), S. wadayamensis (WS-3442-D), S. chartreusis (SF 1623), S. heteromorphus and S. panayensis (C2081X); S. cinnamonensis, S. fimbriatus, S. halstedii, S. rochei and S. viridochromogenes (cephamycins A, B); S. cattleya (thienamycin); and S. olivaceus, S. flavovirens, S. flavus, S. fulvoviridis, S. argenteolus, and S. sioyaensis (MM 4550 and MM 13902).

Preferred host cells of restrictionless strains of Streptomyces taxa that produce polyether antibiotics and in which the present vectors are especially useful and can be transformed, include restrictionless cells of, for example: *S. albus* (A204, A28695A and B, salinomycin), *S. hygroscopicus* (A218, emericid, DE3936), A120A, A286-95A and B, etheromycin, dianemycin), *S. griseus* (grisorixin), *S. conglobatus* (ionomycin), *S. eurocidicus* var. *asterocidicus* (laidlomycin), *S. lasaliensis* (lasalocid), *S. ribosidificus* (lonomycin), *S. cacaoi* var. *asoensis* (lysocellin), *S. cinnamonensis* (monensin), *S. aureofaciens* (narasin), *S. gallinarius* (RP 30504), *S. longwoodensis* (lysocellin), *S. flaveolus* (CP38936), *S. mutabilis* (S-11743a), and *S. violaceoniger* (nigericin).

Preferred host cells of restrictionless strains of Streptomyces taxa that produce glycopeptide antibiotics and in which the present vectors are especially useful and can be transformed, include restrictionless cells of, for example: *S. orientalis* and *S. haranomachiensis* (vancomycin); *S. candidus* (A-35512, avoparcin), *S. eburosporeus* (LL-AM 374), and *S. toyocaensis* (A47934).

Preferred host cells of other Streptomyces restrictionless strains in which the present vectors are especially useful and can be transformed, include restrictionless cells of, for example: *S. coelicolor, S. granuloruber, S. roseosporus, S. lividans, S. tenebrarius, S. acrimycins, S. glaucescens, S. parvilin, S. pristinaespiralis, S. violaceoruber, S. vinaceus, S. virginiae, S. espinosus,* and *S. azureus*.

In addition to the representative Streptomyces host cells described above, the present vectors are also useful and can be transformed into cells of restriotionless strains of other taxa such as, for example: Bacillus, Staphylococcus and related Actinomycetes, including Streptosporangium, Actinoplanes, Nocardia, and Micromonospora. Thus, the vectors of the present invention have wide application and are useful and can be transformed into host cells of a variety of organisms.

While all the embodiments of the present invention are useful, some of the present recombinant DNA cloning vectors and transformants are more preferred than others. Accordingly, preferred vectors are plasmids pFJ127, pFJ277, pFJ141, pFJ142, pFJ278, pFJ282, pFJ291, and pFJ295; and preferred transformants are *Streptomyces ambofaciens*/pFJ127, *S. ambofaciens*/pFJ277, *E. coli* K12 HB101/pFJ141, *S. ambofaciens*/pFJ141, *E. coli* K12 HB101/pFJ142, *S. ambofaciens*/pFJ142, *S. ambofaciens*/pFJ278, *S. ambofaciens*/pFJ282, *S. ambofaciens*/pFJ291, and *S. ambofaciens*/pFJ295. Moreover, of this preferred group, plasmids pFJ127, pFJ277, pFJ141, pFJ142 and pFJ295, and transformants *S. ambofaciens*/pFJ127, *S. ambofaciens*/pFJ277, *E. coli* K12 HB101/pFJ141, *S. ambofaciens*/pFJ141, *E. coli* K12 HB101/pFJ142, *S. ambofaciens*/pFJ142, and *S. ambofaciens*/pFJ295 are most preferred.

The recombinant DNA cloning vectors and transformants of the present invention have broad utility and help fill the need for suitable cloning vehicles for use in Streptomyces and related organisms. Moreover, the ability of the present vectors to confer resistance to antibiotics that are toxic to non-transformed host cells, also provides a functional means for selecting transformants. This is important because of the practical necessity for determining and selecting the particular cells that have acquired vector DNA. Additional DNA segments, that lack functional tests for their presence, can also be inserted in the present vectors and then transformants containing the non-selectable DNA can be isolated by appropriate antibiotic selection. Such non-selectable DNA segments can be inserted at any site, except within regions necessary for plasmid function, maintainance, and replication, and include, but are not limited to, genes that specify antibiotic modification enzymes, antibiotic resistance, antibiotic biosynthetic, and regulatory genes of all types.

More particularly, a procedure used to select for transformants provides a non-selectable DNA segment that comprises a gene to be inserted in a plasmid such as for example, illustrative plasmid pFJ278, at the central SalI restriction site of the ~1.6 kb BamHI resistance-conferring fragment. Such an insertion inactivates the thiostrepton resistance gene and thus allows for the easy identification of transformants containing the recombinant plasmid. This is done by first selecting for neomycin resistance and then identifying those neomycin resistant transformants that are not resistant to thiostrepton. In a similar manner, insertion of a DNA segment of interest at, for example, the internal BamHI restriction site of the ~3.4 kb BamHI resistance-conferring fragment inactivates the neomycin resistance gene. Thus, transformants carrying this recombinant plasmid also are identified easily by first selecting for thiostrepton resistance and then identifying those thiostrepton resistant transformants that are not resistant to neomycin. Therefore, the ability to select for antibiotic resistance in Streptomyces and related cells allows for the efficient isolation of the extremely rare cells out of billions of cells that contain the particular non-selectable DNA of interest.

The functional test for antibiotic resistance, as described herein above, is also used to locate DNA segments that act as control or biosynthetic elements and direct expression of an individual antibiotic resistance gene. Such segments, including but not limited to, promoters, attenuators, repressors, inducers, ribosomal binding sites, and the like, are used to control the expression of other genes in cells of Streptomyces and related organisms.

The thiostrepton and neomycin resistance-conferring vectors of the present invention are also useful for insuring that linked DNA segments are staby maintained in host cells over many generations. These genes or DNA fragments, covalently linked to the thiostrepton or neomycin resistance-conferring fragment and propagated either in Streptomyces or in the cells of related organisms, are maintained by exposing the transformants to levels of thiostrepton or neomycin that are toxic to non-transformed cells. Therefore, transformants that lose the vector, and consequently any covalently linked DNA, cannot grow and are eliminated from the culture. Thus, the vectors of the present invention can stabilize and maintain any DNA sequence of interest.

The cloning vectors and transformants of the present invention provide for the cloning of genes to improve yields of various products that are currently produced in Streptomyces and related cells. Examples of such products include, but are not limited to, streptomycin, tylosin, cephalosporins, actaplanin, narasin, monensin, apramycin, tobramycin, erythromycin, tetracycline, chloramphenicol, vancomycin, and the like. The present invention also provides selectable vectors that are useful for cloning, characterizing, and reconstructing DNA sequences that code for commercially important proteins such as, for example, human insulin, human proinsulin, glucagon, interferon, human growth hormone, avian growth hormone, bovine growth hormone, porcine growth hormone, interleukin 1 and the like; for enzymatic functions in metabolic pathways leading to commercially important processes and compounds; or for control elements that improve gene expression. These desired DNA sequences include, but are not limited to, DNA that codes for enzymes that catalyze synthesis of derivatized antibiotics such as, for example, streptomycin, cephalosporins, tylosin, actaplanin, narasin, monensin, apramycin, tobramycin, tetracycline, chloramphenicol, erythromycin, and vancomycin derivatives, or for enzymes that mediate and increase bioproduction of antibiotics or other products. The capability for inserting and stabilizing such DNA segments thus allows for increasing the yield and availability of antibiotics that are produced by Streptomyces and related organisms.

*Escherichia coli* K12 HB101/pFJ258 (NRRL B-15262) can be cultured in a number of ways using any of several different media. Carbohydrate sources which are preferred in a culture medium include, for example, molasses, glucose, dextrin, and glycerol, and nitrogen sources include, for example, soy flour, amino acid mixtures, and peptones. Nutrient inorganic salts are also incorporated and include the customary salts capable of yielding sodium, potassium, ammonia, calcium, phosphate, chloride, sulfate, and like ions. As is necessary for the growth and development of other microorganisms, essential trace elements are also added. Such trace elements are commonly supplied as impurities incidental to the addition of other constituents of the medium.

*E. coli* K12 HB101/pFJ258 can be grown under aerobic culture conditions over a relatively wide pH range of about 6.5 to 8 at temperatures ranging from about 25° to 40° C. For the production of plasmid pFJ258 in the greatest quantity, however, it is desirable to start with a culture medium at a pH of about 7.2 and maintain a culture temperature of about 37° C. Culturing the *E. coli* cells under the aforementioned conditions results in a reservoir of cells from which the plasmids are respectively isolated by techniques well known in the art.

The following examples further illustrate and detail the invention disclosed herein. Both an explanation of and the actual procedures for constructing the invention are described where appropriate.

EXAMPLE 1

Culture of *E. coli* K12 HB101/pFJ258 and Isolation of Plasmid pFJ258

The bacterium *E. coli* K12 HB101/pFJ258 (NRRL B-15262) is cultured in LB medium which contains, per liter aqueous solution, 10 g. Bacto tryptone, 5 g. Bacto yeast extract and 10 g. NaCl (pH 7.5) with 25 μg./ml. each of the antibiotics ampicillin and chloramphenicol according to conventional microbiological procedures. After 18 hours incubation, about 0.5 ml. of the culture is transferred to a 1.5 ml. Eppendorf tube and centrifuged for about 15 seconds. Unless otherwise indicated, all the manipulations are done at ambient temperature. The resultant supernatant is carefully removed with a finetip aspirator and the cell pellet is suspended in about 100 μl. of freshly prepared lysozyme solution which contains 2 μg./ml. lysozyme, 50 mM glucose, 10 mM EDTA and 25 mM Tris-HCl (pH 8). After incubation at 0° C. for 30 minutes, about 200 μl. of alkaline SDS (sodium dodecyl sulfate) solution (0.2N NaOH, 1% SDS) is added and the tube gently vortexed and the maintained at 0° C. for 15 minutes. Next, about 150 μl of 3M sodium acetate is added and the contents of the tube are mixed gently by inversion for a few seconds.

The tube is maintained at 0° C. for 60 minutes and then centrifuged for 20 minutes at 15,000 rpm to yield an almost clear supernatant. The supernatant is transferred to a second centrifuge tube and the DNA is extracted with phenol:chloroform (24:1) and chloroform. Two volumes of cold ethanol are then added to the aqueous phase to precipitate the DNA. The DNA is raised in 1 ml. of 1/10 TE (Tris-HCl:EDTA (10:1)).

EXAMPLE 2

Construction of Plasmid pLR2

A. HindIII Digestion of Plasmid pIJ6

About 20 μl. (20 μg.) of plasmid pIJ6 DNA, disclosed in Thompson et al., 1980, Nature. 286:525, 5 μl. BSA(-Bovine Serum albumin, 1 mg./ml.), 19 μl. water, 1 μl. of HindIII (containing 3 New England Bio Labs units) restriction enzyme*, and 5 μl. reaction mix** were incubated at 37° C. for 2 hours. The reaction was terminated by the addition of about 50 μl. of 4M ammonium acetate and 200 μl. of 95% ethanol. The resultant DNA precipitate was washed twice in 70% ethanol, dried in vacuo, suspended in 20 μl. of 1/10 TE buffer, and frozen at −20° C. for storage.

*Restriction enzymes and instructions can be obtained from the following sources:
 New England Bio Labs., Inc.
 32 Tozer Road
 Beverly, Massachusetts 01915
 Boehringer-Mannheim Biochemicals
 7941 Castleway Drive
 P.O. Box 50816
 Indianapolis, Indiana 46250
 Bethesda Research Laboratories Inc.
 8717 Grovemont Circle
 P.O. Box 577
 Gaithersburg, Maryland 20760
**Reaction mix for HindIII restriction enzyme was prepared with the following composition.
 600 mM NaCl
 100 mM Tris-HCl, pH 7.9
 70 mM MgCl$_2$
 10 mM Dithiothreitol B. HindIII Digestion of Plasmid pBR322

About 8 μl. (4 μg.) of plasmid pBR322 DNA, 5 μl. reaction mix, 5 μl. BSA (1 mg./ml.), 31 μl. water, and 1 μl. of HindIII restriction enzyme were incubated at 37° C. for 2 hours. After the reaction was terminated by incubating at 60° C. for 10 minutes, about 50 μl. of ammonium acetate and 200 μl. of 95% ethanol were added. The resultant DNA precipitate was washed twice in 70% ethanol, dried in vacuo, and suspended in 45 μl. of water.

C. Ligation of HindIII Digested Plasmids pIJ6 and pBR322

About 20 μl. of HindIII treated plasmid pIJ6 (from Example 2A), 20 μl. of HindIII treated plasmid pBR322 (from Example 2B), 5 μl. BSA (1 mg./ml.), 1 μl. of T4 DNA ligase*, and 5 μl. ligation mix** were incubated at 16° C. for 4 hours. The reaction was terminated by the addition of about 50 μl. 4M ammonium acetate and 200 μl. of 95% ethanol. The resultant DNA precipitate was washed twice in 70% ethanol, dried in vacuo, and suspended in 1/10 TE buffer. The suspended DNA constituted the desired plasmid pLR2.

*T4 DNA ligase and instructions can be obtained from the following sources:
 New England Bio Labs., Inc.
 32 Tozer Road
 Beverly, Massachusetts 01915
 Bethesda Research Laboratories P.O. Box 577
Gaithersburg, Maryland 20760
**Ligation mix was prepared with the following composition.
500 mM Tris-HCl, pH 7.8
200 mM Dithiothreitol
100 mM MgCl$_2$
10 mM ATP

EXAMPLE 3

Construction of E. coli K12 HB101/pLR2

About 10 ml. of frozen competent E. coli K12 HB101 cells (Bolivar et al., 1977, Gene 2:75-93) were pelleted by centrifugation and then suspended in about 10 ml. of 0.01M sodium chloride. Next, the cells were pelleted again, resuspended in about 10 ml. of 0.03M calcium chloride, incubated on ice for 20 minutes, pelleted a third time, and finally, resuspended in 1.25 ml. of 0.03 M calcium chloride. The resultant cell suspension was competent for subsequent transformation.

Plasmid pLR2 in TE buffer (prepared in Example 2C) was ethanol precipitated, suspended in 150 µl. of 30 mM calcium chloride solution, and gently mixed in a test tube with about 200 µl. of competent E. coli K12 HB101 cells. The resultant mixture was incubated on ice for about 45 minutes and then at 42° C. for about 1 minute. Next, about 3 ml. of L-broth (Bertani, 1951, J. Bacteriology 62:293) containing 50 µg./ml. of ampicillin was added. The mixture was incubated with shaking at 37° C. for 1 hour and then plated on L-agar (Miller, 1972, Experiments in Molecular Genetics, Cold Spring Harbor Labs, Cold Spring Harbor, N.Y.) containing ampicillin. Surviving colonies were selected and tested for the expected phenotype (Amp$^R$, Tet$^S$), and constituted the desired E. coli K12 HB101/pLR2 transformants.

EXAMPLE 4

Construction of Plasmid pLR1

Plasmid pLR1 was prepared in substantial accordance with the teaching of Example 2A-C except that plasmid pIJ2, disclosed in Thompson et al., 1980, Nature 286:525, was used in place of plasmid pIJ6. The desired plasmid pLR1 was suspended in 1/10 TE buffer.

EXAMPLE 5

Construction of E. coli K12 HB101/pLR1

The desired construction was carried out in substantial accordance with the teaching of Example 3 except that plasmid pLR1, rather than plasmid pLR2, was used for transformation. Surviving colonies were selected and tested for the expected phenotype (Amp$^R$, Tet$^S$), and constituted the desired E. coli K12 HB101/pLR1 transformants.

EXAMPLE 6

Construction of Plasmid pLR4

A. Partial BamHI Digestion of Plasmid pLR1

About 10 µl (10 µg.) of plasmid pLR1, 5 µl. BSA (1 mg./ml.), 29 µl. water, 1 µl. of BamHI (diluted 1:4 with water) restriction enzyme, and 5 µl. reaction mix* were incubated at 37° C. for 15 minutes. The reaction was terminated by the addition of about 50 µl. of 4M ammonium acetate and 200 µl. of 95% ethanol. The resultant DNA precipitate was washed twice in 70% ethanol, dried in vacuo, and suspended in 20 µl. water.
*Reaction mix for BamHI restriction enzyme was prepared with the following composition.
1.5 M NaCl
60 mM Tris-HCl, pH 7.9
60 mM MgCl$_2$

BamHI Digestion of Plasmid pBR322

The desired digestion was carried out in substantial accordance with the teaching of Example 2B except that BamHI restriction enzyme was used in place of HindIII restriction enzyme. The digested plasmid pBR322 was suspended in 29 µl. of water.

C. Ligation of Partial BamHI Digested Plasmid pLR1 and BamHI Digested Plasmid pBR322

The desired ligation was carried out in substantial accordance with the teaching of Example 2C. The resultant ligated DNA was suspended in TE buffer and constituted the desired plasmid pLR4.

EXAMPLE 7

Construction of E. coli K12 HB101/pLR4

The desired construction was carried out in substantial accordance with the teaching of Example 3 except that plasmid pLR4, rather than plasmid pLR2, was used for transformation. Surviving colonies were selected and tested for the expected phenotype (Amp$^R$, Tet$^S$), and constituted the desired E. coli K12 HB101/pLR4 transformants.

EXAMPLE 8

Construction of Plasmid pFJ127

A. Isolation of ~3.64 kb SalI-ClaI Fragment of pFJ258

About 20 µg. of plasmid pFJ258 DNA, 10 µl. reaction mix*, 10 µl. BSA (1 mg./ml.) 39 µl. water, and 1 µl. of SalI restriction enzyme (containing excess New England Bio Lab units) is incubated at 37° C. for about 15 minutes. After adding an equal volume of 4M ammonium acetate and 2 volumes of 95% ethanol, the mixture is cooled at −20° C. for about 18 hours to precipitate the DNA. The DNA precipitate is collected by centrifugation, rinsed in 70% ethanol, dried in vacuo, and then suspended in about 20 µl. of TE buffer. Following addition of about 10 µl. of ClaI reaction mix**, 10 µl. BSA (1 mg./ml.), 9 µl. water, and 1 µl. of ClaI restriction enzyme (containing excess New England Bio Lab units), the mixture is incubated at 37° C. for about 60 minutes. An equal volume of 4M ammonium acetate and 5 volumes of 95% ethanol is added and then the mixture is cooled at −20° C. for about 18 hours to precipitate the DNA. The DNA precipitate is collected by centrifugation and the desired SalI-ClaI fragments are separated and isolated conventionally by agarose gel electrophoresis in substantial accordance with the teaching of Maniatis et al., 1982 Molecular Cloning, Cold Spring Harbor Laboratories, Cold Spring Harbor, N. Y. Following isolation, the fragment is resuspended in about 20 µl. of 1/10 TE buffer for subsequent ligation.
Reaction mix for SalI restriction enzyme was prepared with the following composition.
1.5 mM NaCl
60 mM Tris-HCl, pH 7.9
60 mM MgCl$_2$
60 mM 2-mercaptoethanol
**Reaction mix for ClaI restriction enzyme was prepared with the following composition.
500 mM NaCl
60 mM Tris-HCl, pH 7.9
60 mM MgCl$_2$

B. Digestion and Isolation of ~0.46 kb SalI-ClaI Fragment of Plasmid pLR2

The desired digestion is carried out in substantial accordance with the teaching of Example 8A except that plasmid pLR2, rather than plasmid pFJ258, is used. The resultant SalI-ClaI fragments are separated and isolated conventionally by agarose gel electrophoresis (Maniatis, et al., 1982).

C. Ligation

About 20 μl. of SalI-ClaI treated plasmid pFJ258 (from Example 8A), 20 μl. of SalI-ClaI treated plasmid pLR2 (from Example 8B), 5 μl. BSA (1 mg./ml.), 1 μl. of T4 DNA ligase, and 5 μl. ligation mix* are incubated at 16° C. for 4 hours. The reaction is terminated by the addition of about 50 μl. 4M ammonium acetate and about 200 μl. cold 95% ethanol. The mixture is cooled to −20° C. for about 18 hours to precipitate the DNA. The resultant DNA precipitate is washed twice in 70% ethanol, dried in vacuo and suspended in about 50 μl. of P medium (Hopwood and Wright, 1978, J. Molecular and General Genetics 162:307) for subsequent transformation. The suspended DNA constitutes the desired plasmid pFJ127.

Figure 3:
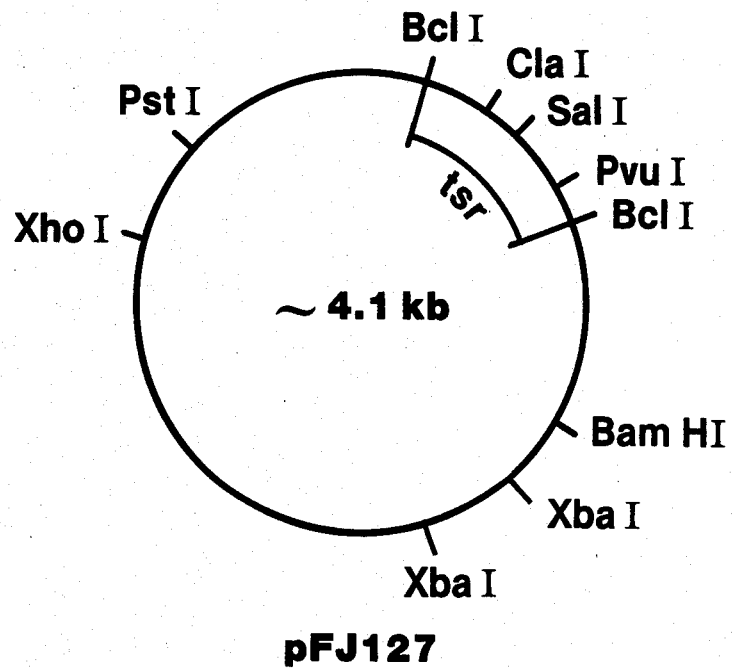
Figure 3:
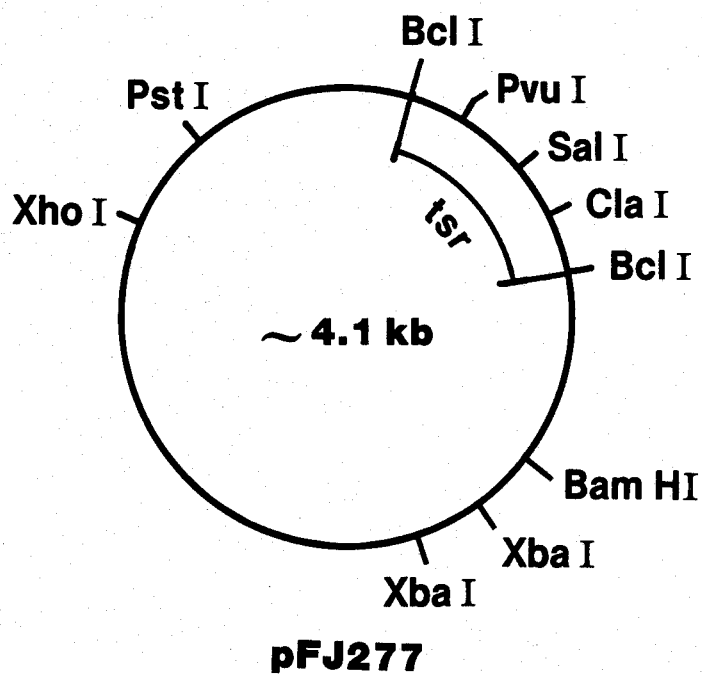

*Ligation mix was prepared with the following composition.
500 mM Tris-HCl, pH 7.8
200 mM Dithiothreitol
100 mM MgCl₂
10 mM ATP Those skilled in the art will recognize and understand that a derivative plasmid of pFJ127 can be constructed wherein the thiostrepton resistance-conferring fragment is in the reverse orientation. Plasmid pFJ277 can be constructed by digesting plasmid pFJ127 with BclI restriction enzyme and subsequently ligating the BclI digested fragments to concomitantly produce plasmids pFJ277 and pFJ127. A restriction site map of plasmids pFJ127 and pFJ277 is presented in FIG. 3 of the accompanying drawings.

EXAMPLE 9

Construction of *Streptomyces ambofaciens*/pFJ127 and *S. ambofaciens*/pFJ277

About 1 μg. of the DNA from Example 8C and 100 μl. of protoplasts of *Streptomyces ambofaciens*, a strain deposited and made part of the permanent stock culture collection of the Northern Regional Research Laboratory, Peoria, Ill., from which it is available to the public under the accession number NRRL 2420, were mixed with 0.5 ml. 20% PEG (polyethylene glycol) in P medium. After 2-3 minutes at ambient temperature 4 ml. of P medium was added to the mixture and centrifuged (about 5 mins., 4° C., 15,000 rpm). The pellet was resuspended in 1 ml. of P medium and 100 μl. of the suspension was plated on fresh or dried R2 plates and incubated for 16-24 hours at 30° C. The desired transformants were selected for thiostrepton resistance by overlaying the regenerating protoplasts with R2 medium (Hopwood et al., 1978) top agar containing sufficient thiostrepton to bring the final plate concentration to 50 μg./ml. The resultant *Streptomyces ambofaciens*/pFJ127 and *S. ambofaciens*/pFJ277 thiostrepton resistant colonies were isolated according to known procedures, recultured, and then conventionally identified by restriction enzyme and agarose gel electrophoretic analysis of the constitutive plasmids (Maniatis et al., 1982). The transformant cultures are then used for subsequent production and isolation of their respective plasmids.

EXAMPLE 10

Construction of Plasmids pFJ278 and pFJ279

A. BamHI Digestion of Plasmid pLR4 and Isolation of the ~3.4 kb Neomycin Resistance-Conferring Fragment The desired digestion is carried out in substantial accordance with the teaching of Example 2B except that BamHI restriction enzyme and plasmid pLR4 are used in place of HindIII restriction enzyme and plasmid pBR322. The desired ~3.4 kb BamHI restriction fragment is isolated conventionally from the DNA suspension by agarose gel electrophoresis (Maniatis et al., 1982). Following isolation, the fragment is resuspended in about 20 μl. of 1/10 TE buffer for subsequent ligation.

B. BamHI Digestion of Plasmid pFJ127 and Ligation

This digestion is also carried out in substantial accordance with the procedure of Example 2B except that BamHI restriction enzyme and plasmid pFJ127 are used in place of HindIII restriction enzyme and plasmid pBR322. The ~3.4 kb BamHI neomycin resistance conferring fragment (isolated above) is ligated to the BamHI digested restriction fragment of plasmid pFJ127 in substantial accordance with the teaching of Example 8C.

Figure 4:
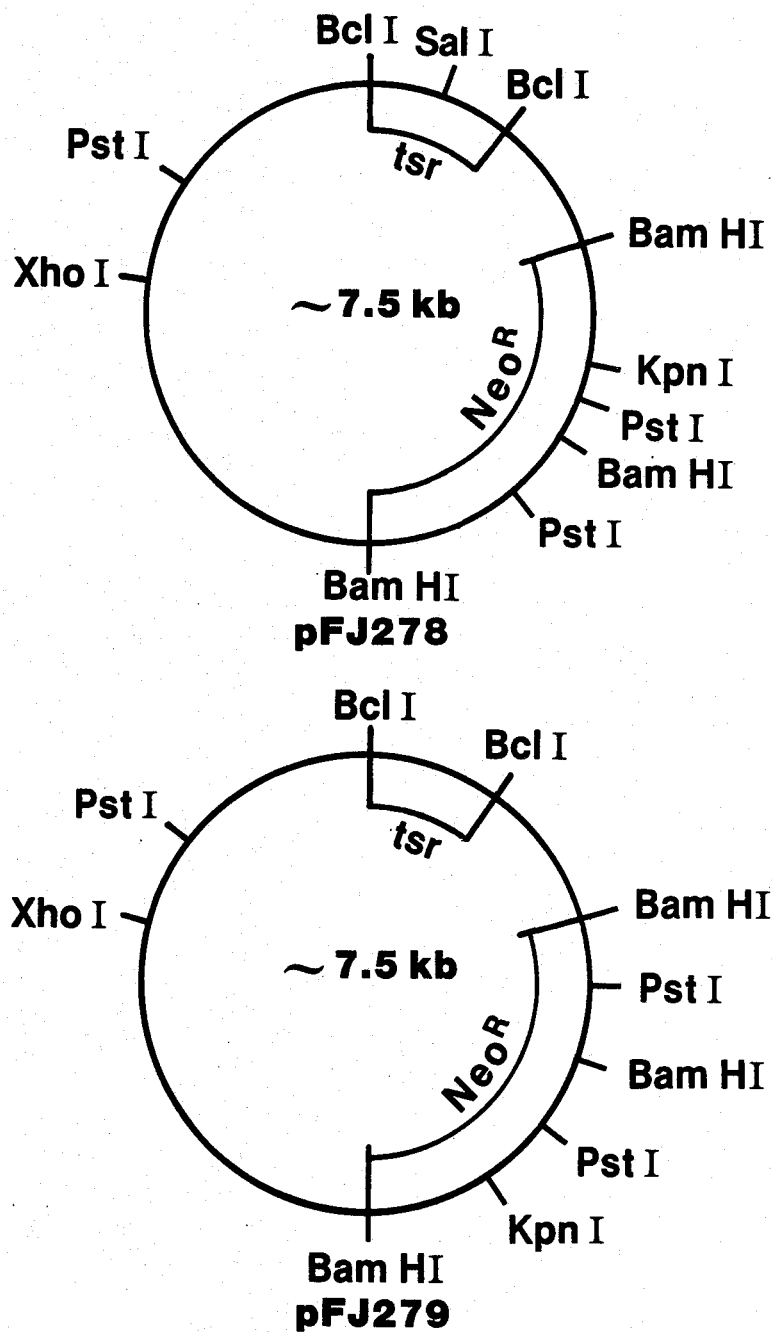

Recombinant plasmids of two orientations result because the ~3.4 kb BamHI resistance-conferring fragment can be oriented in either direction. A restriction site and functional map of plasmids pFJ278 and pFJ279 is presented in FIG. 4 of the accompanying drawings. Those skilled in the art will recognize and understand that additional recombinant plasmids containing the ~2.23 kb XbaI-BclI origin of replication-containing fragments can be generated by the above procedure. These plasmids are functional and thus further exemplify the present invention. The aforementioned plasmids can be conventionally transformed and then identified by restriction enzyme and gel electrophoretic analysis.

EXAMPLE 11

Construction of *Streptomyces ambofaciens*/pFJ278 and *S. ambofaciens*/pFJ279

The desired constructions can be made in substantial accordance with the teaching of Example 9 except that plasmids pFJ278 and pFJ279, rather than plasmids pFJ127 and pFJ277, and the antibiotic neomycin*, rather than thiostrepton, are used for the transformation. The resulting transformants are selected for neomycin resistance by the method described in Example 9 above, except that selection for neomycin resistance is at 1 μg./ml. The resultant *Streptomyces ambofaciens*/pFJ278 and *S. ambofaciens*/pFJ279 neomycin resistant colonies are isolated according to known procedures and then conventionally identified by restriction enzyme and electrophoretic analysis of the constitutive plasmids.

*Antibiotic neomycin can be obtained from Sigma, St. Louis, Mo.

EXAMPLE 12

Construction of Plasmid pFJ282 and *Streptomyces ambofaciens*/pFJ282

A. XbaI Digestion of Plasmid pFJ127

The desired digestion is carried out in substantial accordance with the teaching of Example 8A except that plasmid pFJ127, XbaI restriction enzyme* and reaction mix**, rather than plasmid pFJ258, SalI and ClaI restriction enzymes and reaction mixes, are used. The resultant XbaI fragments are separated and isolated conventionally by agarose gel electrophoresis. Following isolation, the fragment is resuspended in about 20 μl. of 1/10 TE buffer for subsequent ligation.

B. Ligation and Transformation

Figure 5:
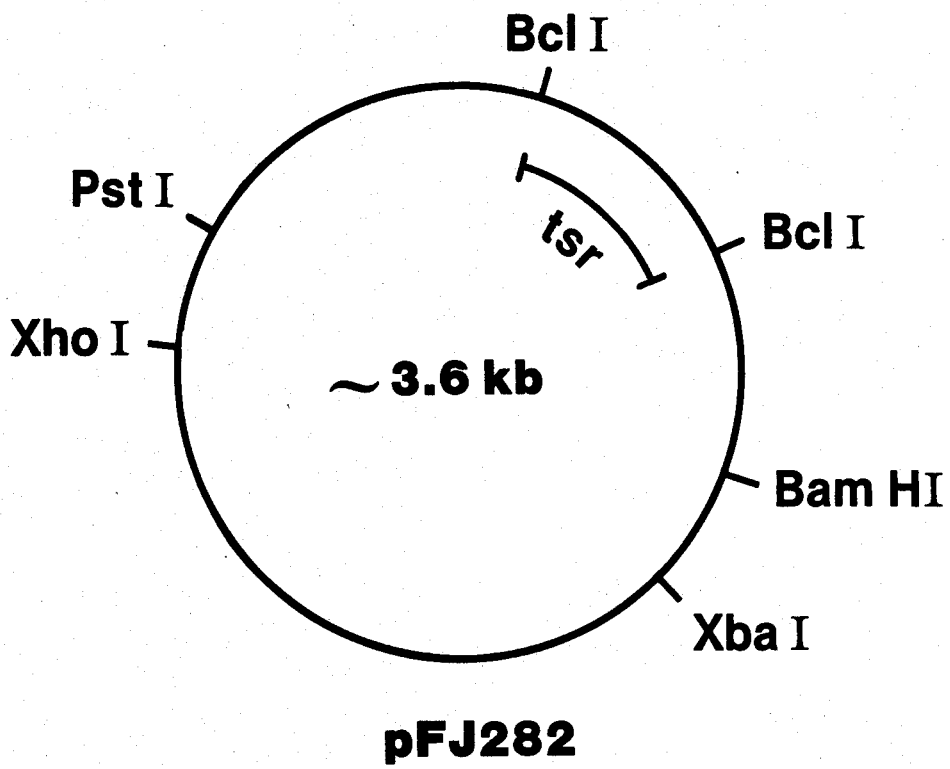

The desired ligation is carried out in substantial accordance with the teaching of Example 8C. The resulting plasmid, pFJ282, carries only one XbaI restriction site and is functional in Streptomyces because it carries the ~2.23 kb XbaI-BclI origin of replication-containing fragment of plasmed pFJ258. A restriction site and functional map of plasmid pFJ282 is presented in FIG. 5 of the accompanying drawings.

The transformant *S. ambofaciens*/pFJ282 is made in substantial accordance with the teaching of Example 9, with the exception that plasmid pFJ282, rather than plasmids pFJ127 and pFJ277, is used for the transformation. The desired transformant is selected for thiostrepton resistance by overlaying the regenerating protoplasts with R2 medium top agar containing sufficient thiostrepton to bring the final plate count concentration to 50 μg./ml. The resultant *Streptomyces ambofaciens*/pFJ282 thiostrepton resistant colonies are isolated according to known procedures and then conventionally identified by restriction enzyme and electrophoretic analysis of the constitutive plasmids.

*XbaI restriction enzyme and information can be obtained from the sources cited in Example 2.
**Reaction mix for XbaI restriction enzyme was prepared with the following composition.
  500 mM NaCl
  60 mM Tris-HCl, pH 7.9
  60 mM $MgCl_2$

EXAMPLE 13

Construction of Bifunctional Plasmids pFJ141 and pFJ142

A. Partial BclI Digestion of Plasmid pFJ127

About 40 μl. (~40 μg.) of plasmid pFJ127 DNA, 10 μl. BSA (1 mg./ml.), 39 μl. water, 1 μl. of BclI (diluted 1:3 with water) restriction enzyme and 10 μl. of reaction mix* were incubated at 50° C. for 15 minutes. The reaction was terminated by the addition of an equal volume of 4M ammonium acetate and 5 volumes of 95% ethanol. The mixture was cooled at −20° C. for about 18 hours to precipitate the DNA. The DNA precipitate was collected by centrifugation, rinsed in 70% ethanol, dried in vacuo, and then suspended in about 50 μl. of 1/10 TE buffer.

*Reaction mix for BclI restriction enzyme was prepared with the following composition.
  750 mM KCl
  60 mM Tris-HCl, pH 7.4
  100 mM $MgCl_2$
  10 mM Dithiothreitol

B. BamHI Digestion of Plasmid pBR328

About 2 μl. (~2 μg.) of plasmid pBR328 DNA, 2.5 μl. BSA (1 mg./ml.), 16 μl. water, 2 μl. of BamHI restriction enzyme, and 2.5 μl. of reaction mix were incubated at 37° C. for 2 hours. After the reaction was terminated by incubating at 60° C. for 10 minutes, about 25 μl. of 4M ammonium acetate and about 100 μl. of 95% ethanol were added. The resultant DNA precipitate was washed twice in 70% ethanol, dried in vacuo, and suspended in about 10 μl. of water.

C. Ligation of Partial BclI Digested Plasmid pFJ127 and BamHI Digested Plasmid pBR328

Figure 6:
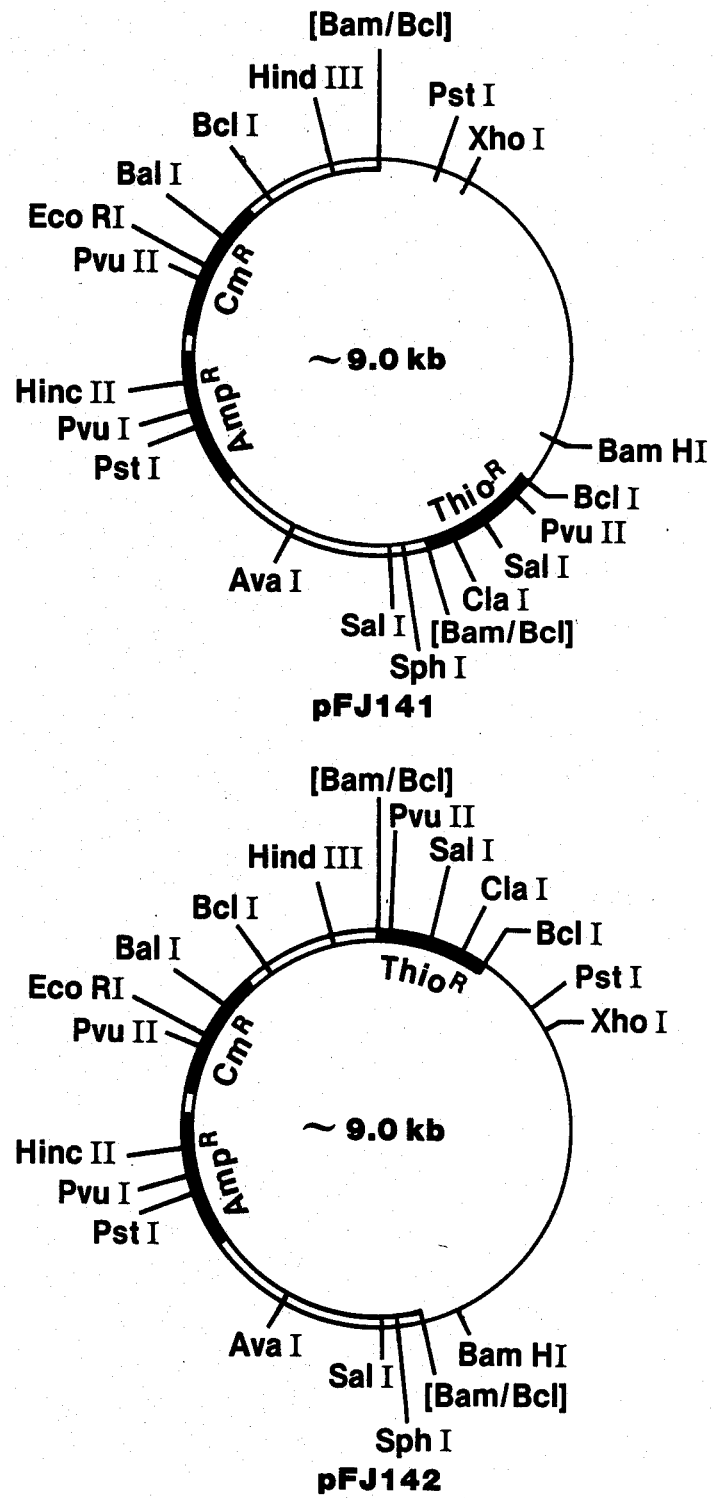

About 20 μl. of partial BclI treated plasmid pFJ127 (from Example 13A), 20 μl. of BamHI treated plasmid pBR328 (from Example 13B), 5 μl. BSA (1 mg./ml.), 15 μl. water, 4 μl. of T4 DNA ligase, and 5 μl. of ligation mix were incubated overnight at 16° C. The reaction was terminated by the addition of about 50 μl. 4M ammonium acetate and 200 μl. of 95% ethanol. The resultant DNA precipitate was washed twice in 70% ethanol, dried in vacuo, and suspended in 1/10 TE buffer. The suspended DNA constituted the desired plasmids pFJ141 and pFJ142. Recombinant plasmids of two orientations result because the restricted plasmid pBR328 can be oriented in either direction. A restriction site and functional map of each of plasmids pFJ141 and pFJ142 is presented in FIG. 6 of the accompanying drawings.

EXAMPLE 14

Construction of *E. coli* K12 HB101/pFJ141 and *E. coli* K12 HB101/pFJ142

The desired constructions were made in substantial accordance with the teaching of Example 3 with the exception that plasmids pFJ141 and pFJ142, rather than plasmid pLR2, are used for the transformation. Surviving colonies were first selected, and tested for the expected phenotype ($Amp^R$, $Cm^R$, $Tet^S$), and then conventionally identified as the desired *E. coli* K12 HB101/pFJ141 and *E. coli* K12 HB101/pFJ142 transformants by restriction enzyme and gel electrophoretic analysis of the constitutive plasmids.

EXAMPLE 15

Construction of *Streptomyces ambofaciens*/pFJ141 and *S. ambofaciens*/pFJ142

The desired constructions were made in substantial accordance with the teaching of Example 9 with the exception that plasmids pFJ141 and pFJ142 rather than plasmids pFJ127 and pFJ277 were used for the transformation. The resulting transformants were selected for thiostrepton resistance by the method described in Example 9 above. The thus constructed thiostrepton resistant *Streptomyces ambofaciens*/pFJ141 and *S. ambofaciens*/pFJ142 colonies were isolated according to known procedures and then conventionally identified by restriction enzyme and electrophoretic analysis of the constitutive plasmids.

EXAMPLE 16

Construction of Plasmids pFJ291 and pFJ292

Most *E. coli* K12 strains methylate certain residues in their DNA. For example, a methylase specified by the dam gene methylates at the N6 position of the indicated adenine in the DNA sequence $5'GA^{me}TC3'$. This methylation has been shown to interfere with cleavage of DNA by some (but not all) restriction endonucleases whose recognition sequences comprise or include the methylated sequences. BclI, a restriction enzyme commonly used in this invention, will not cleave the BclI recognition sequence 5'TGATCA3' if it has been methylated. To avoid this problem, plasmid pFJ258 should be transferred to an *E. coli dam*⁻ strain such as GM48, a strain deposited and made part of the permanent stock culture collection of the Northern Regional Research Laboratory. Peoria, Ill. The strain is available to the public under the accession number NRRL B-15725.

A. Isolation of the ~2.85 kb BamHI-BclI Fragment of Plasmid pFJ258 and Subsequent Digestion with XbaI Restriction Enzyme About 5 μg. of plasmid pFJ258 DNA is treated with BamHI and BclI restriction enzymes* in substantial accordance with the respective teaching of Examples 2A and 13A. An ~2.85 kb fragment that contains the plasmid pFJ258 origin of replication-containing fragment can be recovered by conventional procedures.

About 5 μg. of the isolated ~2.85 kb fragment is subsequently treated with XbaI restriction enzyme* in substantial accordance with the teaching of Example 12A. The XbaI digested fragments can be recovered by conventional procedures.
*Restriction enzymes are readily available from the sources cited in Example 2.

B. Ligation and Final Construction

The desired construction is conveniently done by adding the ~3.4 kb BamHI digested neomycin resistance-conferring fragment of plasmid pLR1 or pLR4 (isolated in Example 10A) to the XbaI digested fragments isolated above by use of T4 DNA ligase. Ligation is performed in substantial accordance with the teaching of Example 8C.

Figure 7:
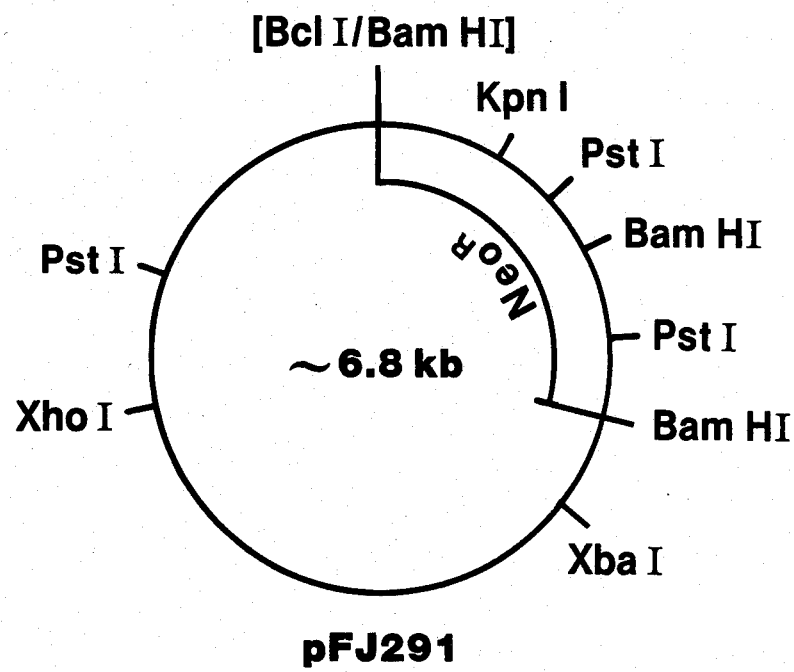
Figure 7:
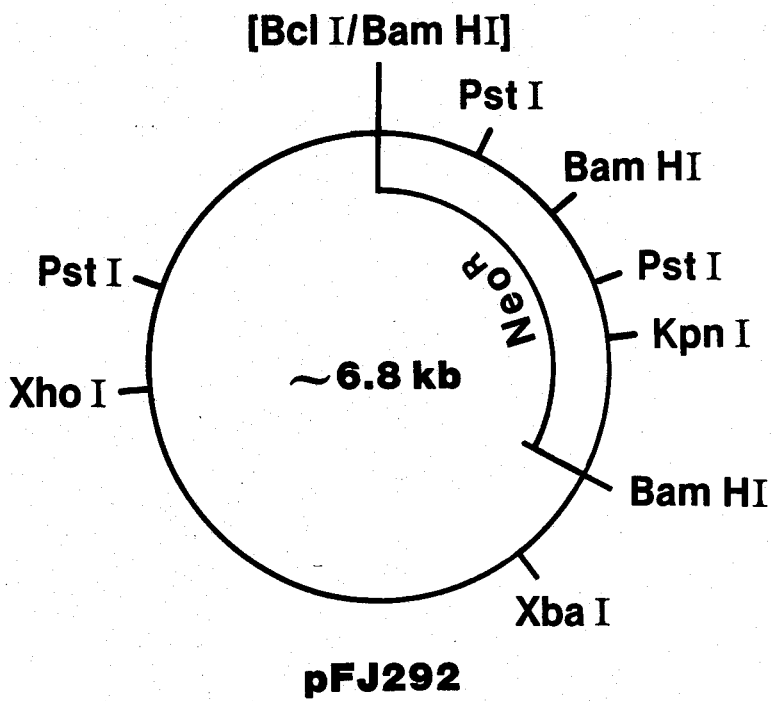

As explained in Examples 8 and 10, plasmids of two orientations result depending upon the orientation of the inserted resistance-conferring fragment. Plasmids pFJ291 and pFJ292 contain the origin of replication-containing fragment of plasmid pFJ258 but will be modified such that a unique XbaI restriction site is present in the plasmids. A restriction site map of plasmids pFJ291 and pFJ292 is presented in FIG. 7 of the accompanying drawings.

EXAMPLE 17

Construction of *Streptomyces ambofaciens*/pFJ291 and *S. ambofaciens*/pFJ292

The desired constructions are made in substantial accordance with the teaching of Example 9 with the exception that plasmids pFJ291 and pFJ292, rather than plasmids pFJ127 and pFJ277, are used for the transformation.

EXAMPLE 18

Construction of Plasmids pFJ295 and pFJ296 and Transformants *S. ambofaciens*/pFJ295 and *S. ambofaciens*/pFJ296

A. Isolation of the ~2.23 kb XbaI-BclI Fragment of Plasmid pFJ258

For the reason specified in the preamble of Example 16, plasmid pFJ258 DNA should first be transferred to an *E. coli dam*⁻ strain, such as *E. coli* GM48, NRRL B-15725, prior to treatment with restriction enzymes. After such transfer about 5 μg. of plasmid pFJ258 DNA is treated with XbaI and BclI restriction enzymes* in substantial accordance with the respective teaching of Examples 12A and 13A. An ~2.23 kb origin of replication-containing fragment from plasmid pFJ258 can be recovered by conventional procedures.
*Restriction enzymes can be readily obtained from the sources cited in Example 2.

B. Ligation and Final Construction

The desired construction is conveniently done by adding a synthetic XbaI-BclI DNA linker* to the ~2.23 XbaI-BclI fragment and then ligating the thus modified fragment to BclI treated plasmid pFJ127 (prepared in substantial accordance with the teaching of Example 10B except that BclI restriction enzyme, rather than BamHI restriction enzyme, is used) by use of T4 DNA ligase. XbaI and BclI restriction and T4 DNA ligase enzymes are available from the sources cited in Example 2. After the ~2.23 kb XbaI-BclI fragment is provided with the XbaI-BclI linker, the ligation of the BclI treated fragment of pFJ127 to form plasmids pFJ295 and pFJ296 is carried out in substantial accordance with the teaching of Example 8C. The subsequent transformation into *S. ambofaciens* to form *S. ambofaciens*/pFJ295 and *S. ambofaciens*/pFJ296 is carried out according to the teaching of Example 9. As explained in Examples 8 and 10, plasmids of two orientations result depending upon the orientation of the inserted thiostrepton resistance-conferring fragment.
*XbaI-BclI and other linkers are available from
New England Bio Labs., Inc.
32 Tozer Road
Beverly, Massachusetts 01915 and are discussed in Crea et al., 1978, Proc. Nat'l Acad. Sci., U.S.A., 75:5765 and Itakura et al., 1977, Science 198:1056.

Representative plasmids and transformants constructed in accordance with the foregoing teaching include the following listed in Tables 1 and 2 below.

TABLE 1

| | | Representative Plasmids | |
|---|---|---|---|
| Example No. | Plasmid Name | ~ Size in kb | Construction |
| 19 | pFJ277 | 4.1 | BclI digestion and ligation of pFJ127 (Reverse orientation of pFJ127) |
| 20 | pFJ280 | 6.7 | BclI deletion of pFJ278 |
| 21 | pFJ281 | 6.7 | BclI deletion of pFJ279 |
| 22 | pFJ283* | 7.0 | Ligation of pLR4 ~3.4 BamHI fragment into BamHI digested pFJ282 |
| 23 | pFJ284 | 7.0 | Reverse orientation of pFJ283 |
| 24 | pFJ285* | 12.4 | Ligation of pLR4 ~3.4 BamHI fragment into BamHI digested pFJ141 |
| 25 | pFJ286 | 12.4 | Reverse orientation of pFJ285 |
| 26 | pFJ287* | 12.4 | Ligation of pLR4 ~3.4 BamHI fragment into BamHI digested pFJ142 |
| 27 | pFJ288 | 12.4 | Reverse orientation of pFJ287 |
| 28 | pFJ289 | 11.6 | BclI deletion of pFJ285 |
| 29 | pFJ290 | 11.6 | BclI deletion of pFJ287 |
| 30 | pFJ293+ | 8.4 | Ligation of pLR2 ~1.6 BamHI fragment into BamHI digested pFJ291 |
| 31 | pFJ294 | 8.4 | Reverse orientation of pFJ293 |
| 32 | pFJ297* | 5.6 | Ligation of pLR4 ~3.4 BamHI fragment into ~2.23 kb XbaI-BclI fragment of pFJ258 |
| 33 | pFJ298 | 5.6 | Reverse orientation of pFJ297 |
| 34 | pFJ299* | 6.4 | Ligation of pLR4 ~3.4 BamHI fragment into BclI digested pFJ295 |
| 35 | pFJ300 | 6.4 | Reverse orientation of pFJ299 |
| 36 | pFJ303* | 6.4 | Ligation of pLR4 ~3.4 BamHI fragment into BclI digested pFJ296 |
| 37 | pFJ304 | 6.4 | Reverse orientation of pFJ303 |

*Orientation such that the KpnI site of the pLR4 fragment is closest to the XbaI site of the origin of replication-containing restriction fragment of plasmid pFJ258.
+Orientation such that the ClaI site of the pLR2 fragment is closest to the XbaI site of plasmid pFJ291.

TABLE 2

Representative Transformants

1. Streptomyces R/R[1] wherein R is *ambofaciens, aureofaciens, griseofuscus, fradiae\*, lividans, granuloruber, tenebrarius, cinnamonensis* or *toyocaensis* and wherein R[1] independently is a pFJ plasmid lISted in Table 1.
2. *E. coli* R[2]/R[3] wherein R[2] is K12, K12 HB101 or GM48 and wherein R[3] independently is plasmid pFJ285, pFJ286, pFJ287, pFJ288, pFJ289, or pFJ290.

\*The following procedure is used for transforming *S. fradiae*. Use low OD cells (less than 4 O.O.D. units) grown at 29° C. in the presence of 0.4% glycene in TSB medium. Protoplasts are formed in the presence of 1 mg./ml. lysozyme in P medium on ice followed by two washes with P medium. Chill for 1–3 hours and then warm to ambient temperature.

Mix 0.8 μg. calf thymus DNA and 1.5 μg. protamine sulfate for one minute, then add: purified plasmid DNA (less than 100 μg) suspended in 10 μl. of P medium, 200 μl. of diluted protoplasts (1/3×), 0.9 ml. of 55% PEG 1000 and mix for one minute. Using soft agar overlays, plate protoplasts and incubate at 29° C. for 16–24 hours then overlay with the appropriate antibiotic. Reincubate at 29° C. and score the plates in 7–10 days.

We claim:

1. In a recombinant DNA cloning vector comprising:
   (a) a functional Streptomyces origin of replication-containing restriction fragment, and
   (b) one or more DNA segment that convey resistance to at least one antibiotic when transformed into a sensitive restrictionless host cell that is susceptible to transformation, cell division, and culture and that is selected from the group consisting of *E. coil* and Streptomyces; the improvement which consists of the Streptomyces origin of replication-containing fragment which lies with an ~2.23 kb XbaI-BclI restriction fragment of plasmid pFJ258.

2. The vector of claim 1 wherein the ~2.23 kb XbaI-BclI fragment lies within an ~2.85 kb BamHI-BclI fragment of pFJ258.

3. The vector of claim 1 wherein the ~2.23 XbaI-BclI fragment lies within an ~3.64 kb SalI-BclI fragment of pFJ258.

4. The vector of claim 3 wherein the restriction fragment is the 3.64 kb SalI-BclI restriction.

5. The vector of claim 2 wherein the restriction fragment is the 2.85 kb BamHI-BclI restriction fragment.

6. The vector of claim 1 wherein the restriction fragment is the 2.23 kb XbaI-BclI restriction fragment.

7. The recombinant DNA cloning vector of claim 1 selected from the group consisting of plasmids pFJ127, pFJ277, pFJ278, pFJ279, pFJ280, pFJ281, pFJ282, pFJ283, pFJ284, pFJ291, pFJ292, pFJ293, pFJ294, pFJ295, pFJ296, pFJ297, pFJ298, pFJ299, pFJ300, pFJ303, and pFJ304.

8. The cloning vector of claim 7 which is pFJ127.
9. The cloning vector of claim 7 which is pFJ278.
10. The cloning vector of claim 7 which is pFJ282.
11. The cloning vector of claim 7 which is pFJ291.
12. The cloning vector of claim 7 which is pFJ295.
13. A recombinant DNA cloning vector of claim 39 comprising in addition:
   (c) a functional replicon-containing fragment of an *E. coli* plasmid.

14. The recombinant DNA cloning vector of claim 13 wherein the functional replicon-containing fragment of the *E. coli* plasmid is selected from the group consisting of fragments of plasmids pBR322, pBR325, and pBR328.

15. The recombinant DNA cloning vector of claim 14 which is selected from the group consisting of plasmids pFJ141, pFJ142, pFJ285, pFJ286, pFJ287, pFJ288, pFJ289 and pFJ290.

16. The recombinant DNA cloning vector of claim 15 which is plasmid pFJ141.

17. The recombinant DNA cloning vector of claim 15 which is plasmid pFJ142.

18. A transformed restrictionless host cell which is Streptomyces R/R' wherein R is *ambofaciens, griseofuscus, lividans, fradiae, aureofaciens, tenebrarius, cinnamonensis,* or *toyocaensis* and wherein R' independently is a recombinant DNA cloning vector of claim 7.

19. A transformed restrictionless host cell, selected from the group consisting of Streptomyces and Nocardia, comprising a recombinant DNA cloning vector of claim 1.

20. A transformed restrictionless host cell, selected from the group consisting of Streptomyces, Nocardia, and *E. coil,* comprising a recombinant DNA cloning vector of claim 13.

21. The transformed host cell of claim 19 which is Streptomyces.

22. The transformed host cell of claim 19 which is Nocardia.

23. The transformed host cell of claim 19 in which the recombinant DNA cloning vector is selected from the group consisting of plasmids pFJ127, pFJ277, pFJ278, pFJ279, pFJ280, pFJ281, pFJ282, pFJ283, pFJ284, pFJ291, pFJ292, pFJ293, pFJ294, pFJ295, pFJ296, pFJ297, pFJ298, pFJ299, pFJ300, pFJ303 and pFJ304.

24. The transformed host cell of claim 23 which is restrictionless Streptomyces.

25. The transformed Streptomyces of claim 24 which is *Streptomyces fradiae.*

26. The transformed Streptomyces of claim 24 which is *Streptomyces griseofuscus.*

27. The transformed Streptomyces of claim 24 which is *Streptomyces coelicolor.*

28. The transformed Streptomyces of claim 24 which is *Streptomyces ambofaciens.*

29. The transformed host cell of claim 24 which is *Streptomyces ambofaciens*/pFJ127.

30. The transformed host cell of claim 20 wherein the replicon-containing fragment in the vector is a restriction fragment of plasmid pBR328.

31. The transformed host cell of claim 20 which is *Streptomyces ambofaciens*/pFJ141.

32. The transformed host cell of claim 20 which is *Streptomyces ambofaciens*/pFJ142.

33. The transformed host cell of claim 20 which is *E. coli* K12/pFJ141.

34. The transformed host cell of claim 20 which is *E. coli* K12/pFJ142.

\* \* \* \* \*

UNITED STATES PATENT AND TRADEMARK OFFICE
CERTIFICATE OF CORRECTION

PATENT NO. : 4,643,975
DATED : February 17, 1987
INVENTOR(S) : Jeffrey T. Fayerman, Nancy E. Malin It is certified that error appears in the above—identified patent and that said Letters Patent is hereby corrected as shown below:

Column 3, line 6, "neomyoin" should read --neomycin--.

Column 7, line 32, "restriotionless" should read --restrictionless--.

Column 8, line 44, "staby" should read --stably--.

Column 15, line 23, "plasmed" should read --plasmid--.

Column 19, line 33, "E. coil" should read --E. coli--.

Column 20, line 27, "E. coil" should read --E. coli--.

Signed and Sealed this

First Day of March, 1988

Attest:

DONALD J. QUIGG

Attesting Officer

Commissioner of Patents and Trademarks